United States Patent
Stoop et al.

[11] Patent Number: 6,128,532
[45] Date of Patent: Oct. 3, 2000

[54] PACEMAKER WITH AUTOMATICALLY CONTROLLED VENTRICULAR SAFETY PULSE

[75] Inventors: Gustaaf A. P. Stoop; Bernhard deVries, both of Dieren, Netherlands

[73] Assignee: Vitatron Medical, B.V., Dieren, Netherlands

[21] Appl. No.: 09/153,406

[22] Filed: Sep. 15, 1998

[51] Int. Cl.[7] .......................... A61N 1/362; A61N 1/368
[52] U.S. Cl. ........................... 607/9; 607/28; 607/18
[58] Field of Search .......................... 607/9, 18, 25, 607/28

[56] References Cited

U.S. PATENT DOCUMENTS

| | | |
|---|---|---|
| 4,825,870 | 5/1989 | Mann et al. . |
| 4,974,589 | 12/1990 | Sholder . |
| 5,366,488 | 11/1994 | Franberg . |
| 5,522,857 | 6/1996 | van Krieken ........................... 607/9 |
| 5,713,933 | 2/1998 | Condie et al. ....................... 607/28 |
| 5,713,934 | 2/1998 | Leckrone ............................ 607/28 |
| 5,776,167 | 7/1998 | Levine et al. ......................... 607/9 |
| 5,782,881 | 7/1998 | Lu et al. .............................. 607/9 |
| 5,861,008 | 1/1999 | Obel et al. . |

*Primary Examiner*—Carl H. Layno
*Attorney, Agent, or Firm*—Thomas F. Woods; Michael J. Jaro; Harold Patton

[57] ABSTRACT

There is provided a pacemaker system having the feature of delivering a ventricular safety pulse (VSP) following an early ventricular sense (VS), wherein the pacemaker automatically determines whether VSPs are to be delivered following early VSs, and if yes, with what timing. The pacemaker gathers data following delivered VSPs, which data contains information indicative of whether each early VS was indeed the result of a spontaneous R wave, or was due to crosstalk from a prior delivered atrial pace pulse. This data is processed and, when it presents a high statistical confidence, is used to make a determination of whether to respond with the assumption of a true R wave, or of crosstalk. If the data is not statistically significant, the pacemaker delivers VSPs in a normal fashion, e.g., at the end of a programmable VSP interval timed out following delivery of an atrial pace pulse.

15 Claims, 4 Drawing Sheets assume: crosstalk
indication: ignore VS and deliver normal VP at end of AV_int assume: Real VS
indication: inhibit VSP (c) and (d)
assume: ambiguous
indication: maintain VSP at VSP_int; collect data

PACEMAKER WITH AUTOMATICALLY CONTROLLED VENTRICULAR SAFETY PULSE

FIELD OF THE INVENTION

This invention lies in the field of cardiac dual chamber pacing systems and, more particularly, pacing systems with the provision of delivering a ventricular safety pulse on a sensed ventricular signal which occurs within a short interval following a delivered atrial pulse.

BACKGROUND OF THE INVENTION

The problem of crosstalk in dual chamber pacemakers has been recognized for some time. Crosstalk can occur when an atrial pace pulse (AP) is delivered, and the ventricular sensing electrodes pick up a signal from the atrial pulse before the cardiac conduction system delivers a QRS depolarization wave to the ventricle. When and if this happens, the pacemaker on-demand logic "sees" a ventricular sense, and if it didn't know better the pacemaker would inhibit delivery of a ventricular pace pulse and reset the atrial and ventricular escape intervals. This can have the highly detriment result that the ventricle is not always paced when the atrium is paced.

The pacemaker logic can attempt to distinguish the crosstalk event by recognizing that such a false crosstalk sense occurs before the normal QRS, e.g., a crosstalk sense occurs within about 100 ms after the atrial pace whereas a normal QRS occurs within an AV delay of about 120–200 ms. This distinction could be used by blanking ventricular sensing for about 100 ms, but this has the disadvantage that real ventricular signals, e.g., PVCs or atrial undersensing followed by a true ventricular sense (VS), would not be recognized. Some short blanking interval is necessary following the delivery of an atrial pulse, but in order to detect the maximum amount of information, the shorter the blanking period the better.

Another approach to the problem is that represented by U.S. Pat. No. 4,825,870. In this approach, the pacemaker times out an early interval following an AP, e.g., 64–100 ms. If a "VS" is detected in this interval, the pacemaker times out a shorter AV interval, e.g., 120 ms. If no VS is sensed within this shortened interval, the pacemaker logic does not take a chance, assumes that the sense was crosstalk, and delivers a ventricular safety pulse to be safe. Of course, if a VS does intervene in the shortened AV interval, delivery of a ventricular pulse is inhibited. Various other schemes have been proposed, which establish a crosstalk interval, treat an early sense in the crosstalk interval as noise, and reset the crosstalk interval by a short duration whenever a sense occurs in it, up to a maximum AV interval. In these schemes, generally, a safety pulse will be delivered if consecutive senses are timed at a rate that indicates noise. See, for example, U.S. Pat. No. 5,552,857, assigned to Vitatron Medical B.V., the assignee of this invention.

The above solutions to the crosstalk problem have the disadvantage of not reacting to precise information, and of providing a compromise solution. If a sense is crosstalk, the desireable response is to wait for timeout of the normal AV interval, not to deliver a pulse to the ventricle after timeout of a shortened interval. And if the sense was that of a true R wave, it is better not to deliver a pulse shortly thereafter. It is our observation that generally, if crosstalk is being sensed, the pacemaker can detect a pattern, and treat such early senses as crosstalk, i.e., ignore them; and that if these senses are intrinsic signals, the pacemaker logic should respond appropriately, e.g., by simply re-setting the escape intervals. Accordingly, we base a solution to the crosstalk problem on a technique for obtaining data which, in most cases, establishes the nature of the early senses with a high degree of confidence, so that the pacemaker can respond appropriately.

SUMMARY OF THE INVENTION

It is an object of this invention to establish the nature of early ventricular senses and to automatically determine whether a ventricular safety pulse (VSP) should be delivered following an early ventricular sense after an atrial pulse. The determination is based upon data gathered following early ventricular senses, and analyzing such data to establish whether such senses represented cross talk or intrinsic R waves.

A dual chamber pacemaker is provided, wherein the pacemaker has a data gathering mode during which at least two forms of data are collected which carry information relating to the nature of an early ventricular sense. First, following an early ventricular sense, e.g., one that comes within 100 ms of a delivered atrial pulse, the pacemaker delivers a VSP and then looks to see whether the VSP captured the ventricle. If yes, this indicates that the earlier sense had not been an R wave, and was probably crosstalk. If no, this means that the ventricle was refractory in view of an earlier depolarization, such that the early sense probably was an intrinsic R wave. However, it is noted that techniques for determining capture are not perfect, and so a second form of data is obtained after an early ventricular sense. Following the delivered VSP and the capture detection step, the pacemaker looks for the T wave, and times the QT, or stim-T interval from the VSP to the T wave. The running value of this parameter is known to the pacemaker, and the monitored value is compared to the running value to see if it matches. If there is a QT match, this indicates that the VSP evoked the response, i.e., the VSP indeed did achieve capture; if there is not a match, this indicates that the early sense was an intrinsic beat. There is thus provided redundant information from which the determination can usually be made with a high degree of confidence. The pacemaker collects such data to point where a decision can be made, and then sets its logic to automatically respond appropriately to an early ventricular sense as either crosstalk or an intrinsic beat.

DETAILED DESCRIPTION OF THE PREFERRED EMBODIMENTS

Figure 1:
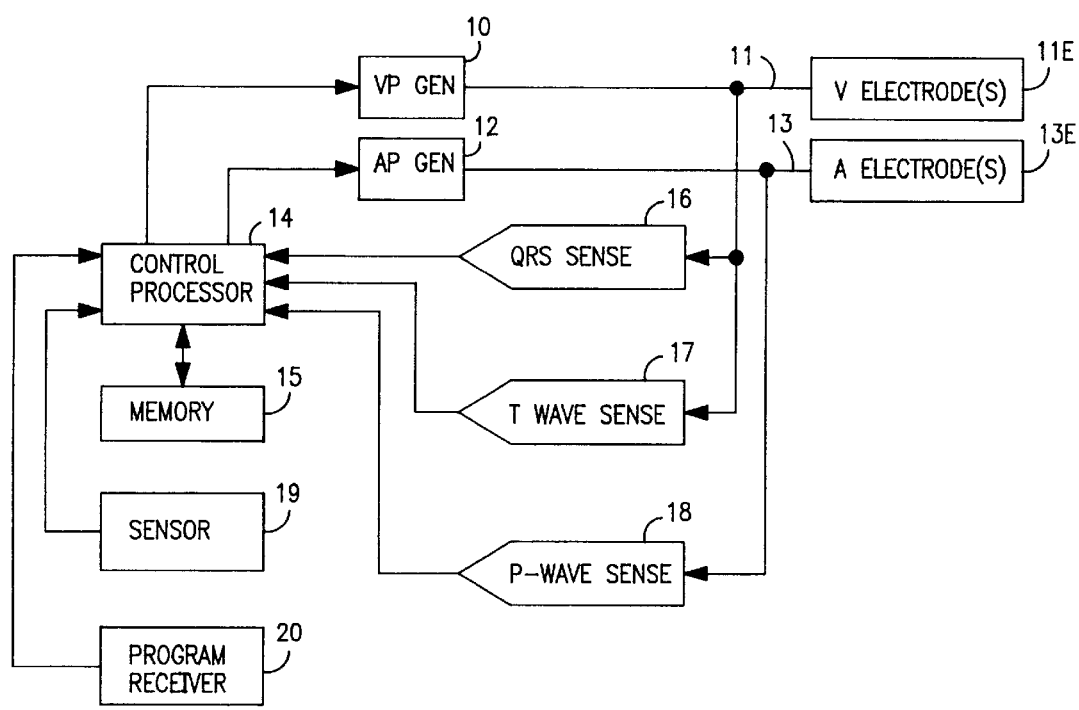
FIG. 1 is a block diagram showing the primary components of a pacemaker in accordance with this invention.

Referring now to FIG. 1, there is shown a block diagram of the primary components of an illustrative pacemaker system which incorporates the features of this invention. A ventricular pace generator 10, controlled by control block 14, generates ventricular pacing pulses and delivers them to the ventricle through a lead 11 which carries one or more ventricular electrodes 11E. Likewise, atrial pacing pulses are generated by generator 12, also under control of block 14, which atrial pacing pulses are delivered through a lead 13 to one or more atrial electrodes 13E. Sensed QRS signals from the ventricular electrodes are processed at QRS sense block 16, and delivered to control block 14. Control block 14 suitably includes a microprocessor, and is interconnected with memory 15. Signals from the ventricular electrodes are also connected to T-wave sense block 17 for picking out T-waves and connecting them to block 14. The T-wave information is used to determined the ongoing value of QT interval, which is used in the routine of FIG. 3 as part of the determination of when an early "VS" has been a real VS or crosstalk. The QT interval is also used as a rate setting parameter in a QT rate responsive pacemaker. Similarly, P-waves picked up by the atrial electrodes are connected to P-wave sense block 18, which provides P-wave signal data to control block 14. A sensor 19, such as an activity sensor, may also be employed for a rate responsive pacemaker, providing an output which is connected to control block 14. Also, programmer receiver 20 may receive data and/or downloaded control software, which is connected to control block 14 and from there may be transferred to memory 15. In the pacemaker system of this invention, the software for the illustrated VSP control routine is suitably stored in dedicated ROM or RAM memory (the control parameters are stored in RAM memory) for use by the microprocessor in determining when and how a VSP is to be delivered when a ventricular signal is sensed within a predetermined VSP interval (VSP_int) following a delivered atrial pulse (AP). The choice of the microprocessor and type and amount of memory is a matter of design choice. Such software control of pacemaker functions is well known in the art and within the skill of pacemaker designers.

Figure 2:
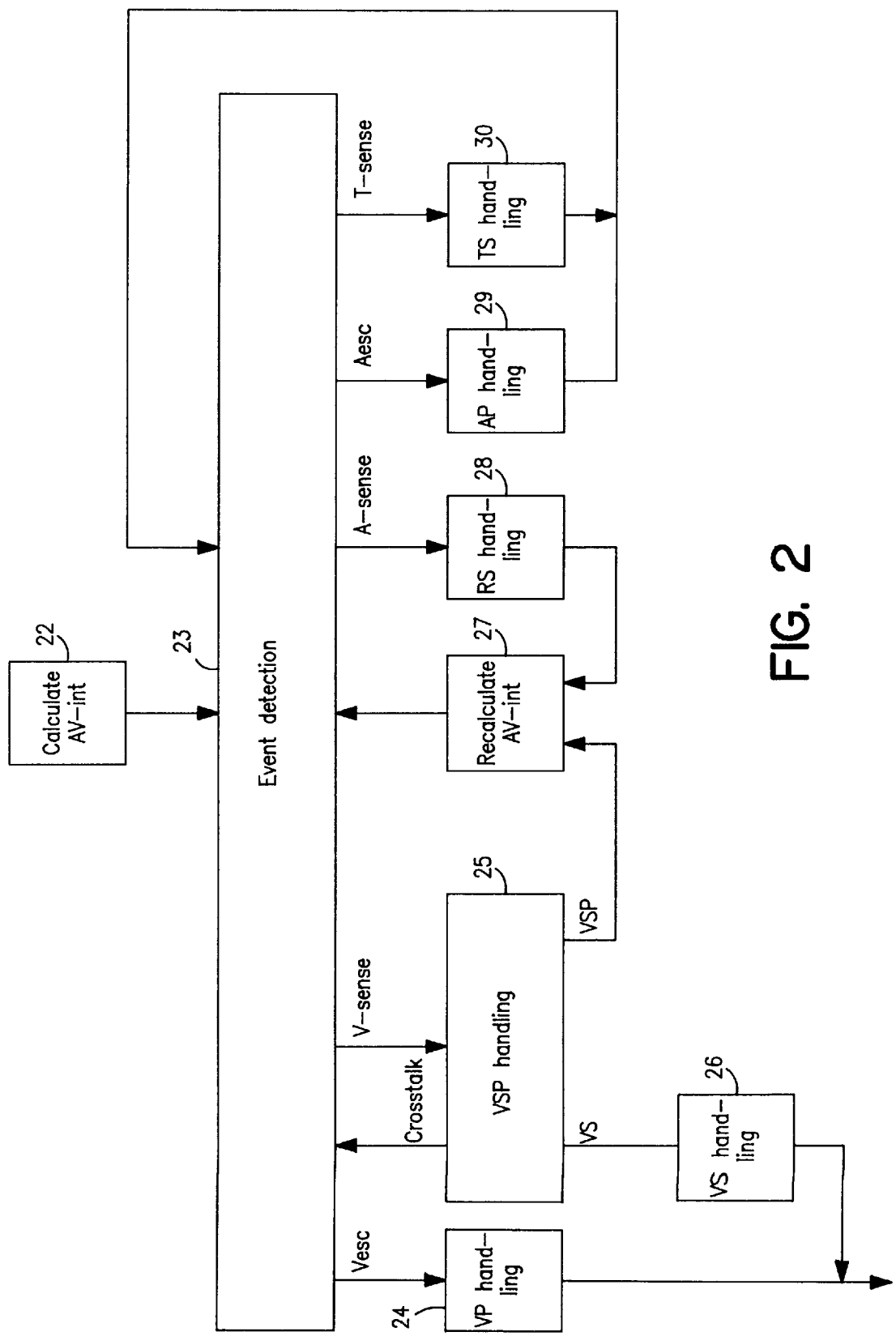
FIG. 2 is a flow diagram illustrating event handling in a pacemaker system in accordance with this invention.

Referring now to FIG. 2, there is shown a simplified flow diagram showing event handling in a pacemaker in accordance with this invention. The steps of this routine are performed every cycle, and control the response of the pacemaker to the various anticipated events. At 22, the pacemaker makes an initial calculation of the AV interval, or AV_int. At 23, the pacemaker detects the event. As is indicated, an event may be an atrial timeout (AESC); a ventricular timeout (VESc); a V-sense; an A-sense; or a T-sense. Other events and situations may also be detected, but are not necessary for an understanding of this invention.

If the event is the timeout of a ventricular escape interval, the pacemaker goes directly to block 24, for ventricular pace (VP) handling, i.e., delivery of a VP to the patient's ventricle. Note that for a dual chamber pacemaker operating in a synchronous mode, the value of the ventricular escape interval is determined by the AV_int which is timed out following the atrial event. If, however, at 23 the event is a V-sense, then the pacemaker goes to block 25 for VSP handling. In this invention, VSP handling means determining whether the V-sense is a normal VS, or whether is has occurred within the VSP interval and if so, whether it is to be treated as crosstalk, whether a VSP is to be delivered, or if it is to be treated as a normal V-sense. If it is determined that this is a normal V-sense, the routine goes to block 26 and carries out VS handling, after which it exits. If, however, the V-sense has occurred during the VSP_int, the VSP handling block determines whether or not it is deemed to be crosstalk, in accordance with prior data on senses that have occurred during the VSP_int, as is discussed more fully in connection with FIG. 3. If it is deemed crosstalk, the routine returns to 23, and the normal AV delay continues, for delivery of a normal VP. Thus, for crosstalk, Vesc is set corresponding to the normal AV delay, and the next event is either a V-sense of a spontaneous ventricular beat, or time out of Vesc and delivery of a VP. On the other hand, if it is determined that the situation calls for delivery of a VSP, then at 27 the AV_int is recalculated to the value of VSP_int, and the routine goes to 23 to await time out of the Vesc.

Still referring to FIG. 2, if at 23 the detected event is an atrial sense, the pacemaker goes to block 28 for AS handling, and then to block 27 for recalculation of AV_int if necessary, and initiation of the AV_int timeout. If the event is an atrial escape, the pacemaker goes to 29 and delivers an atrial pulse. If the event detected is a T wave, the pacemaker goes to block 30 for T-sense handling, e.g., determining the QT interval for determination of crosstalk or a QT rate responsive pacemaker. Following any event other than a ventricular event, the routine returns to block 23 and waits to handle the anticipated ventricular event.

Figure 3:
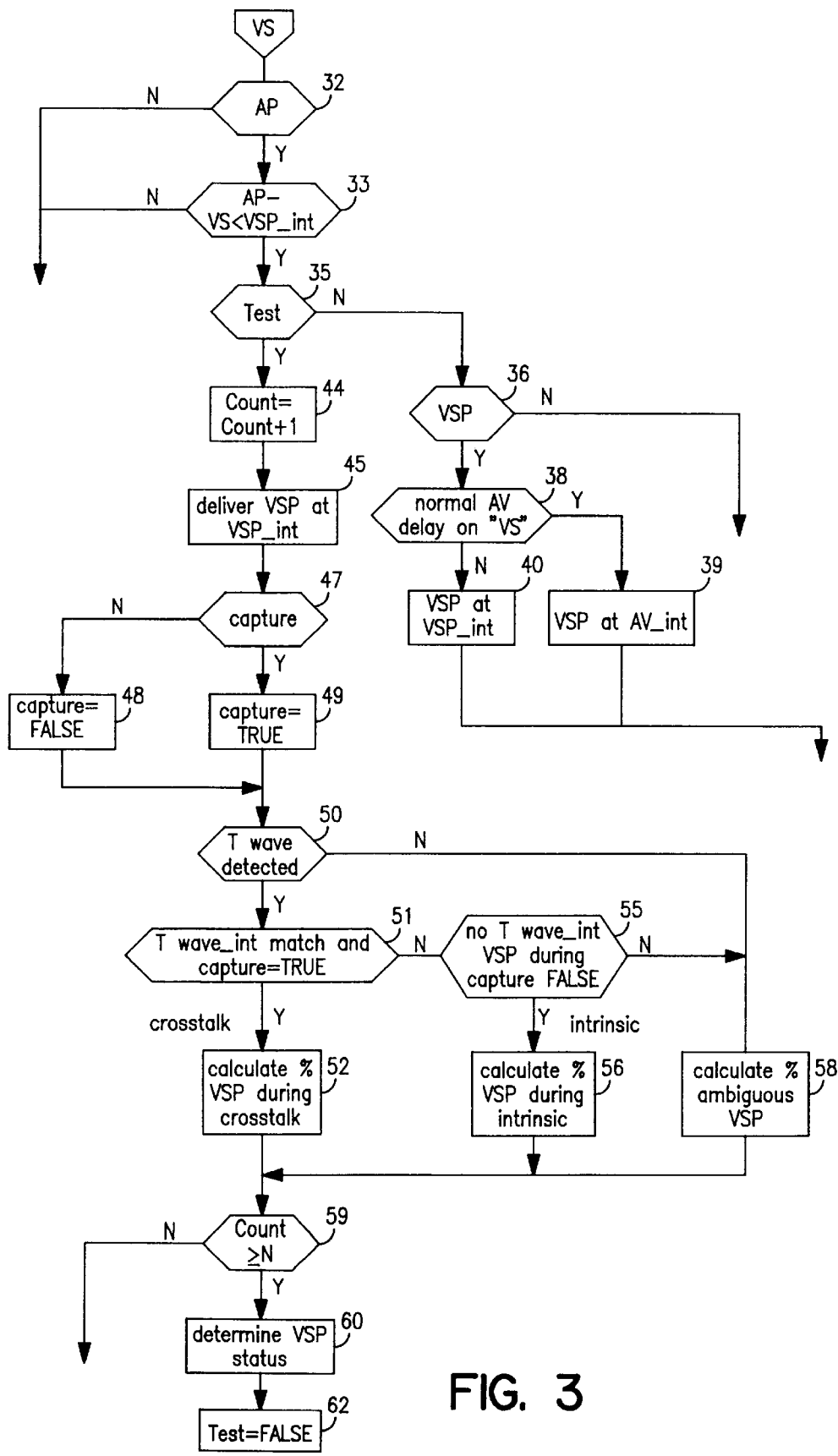
FIG. 3 is a detailed flow diagram showing the primary logic steps taken to determine VSP control in accordance with this invention.
Figure 4A:
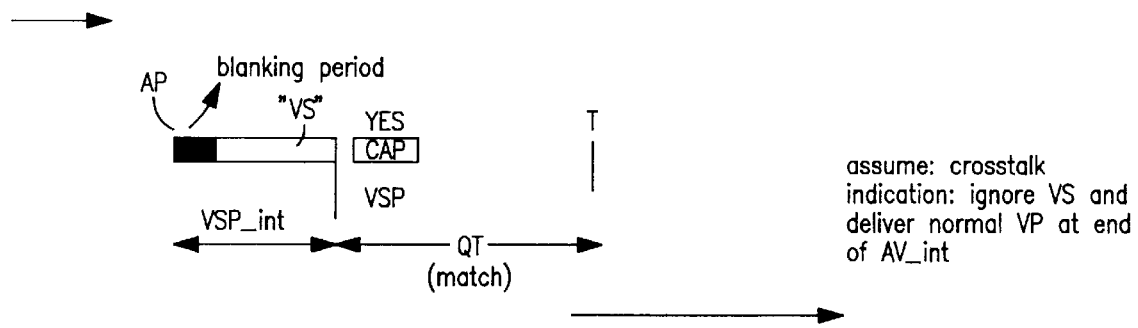
FIGS. 4a, 4b, 4c, 4d are a series of timing diagrams illustrating different situations where a VSP can be delivered.
Figure 4B:
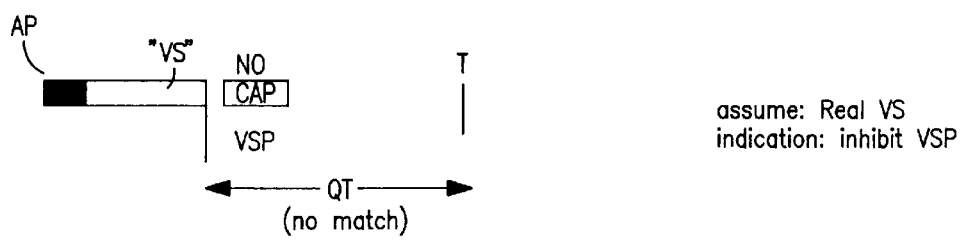
Figure 4C:
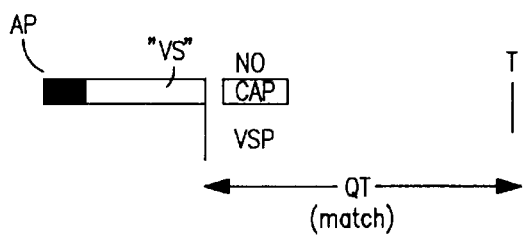
Figure 4D:
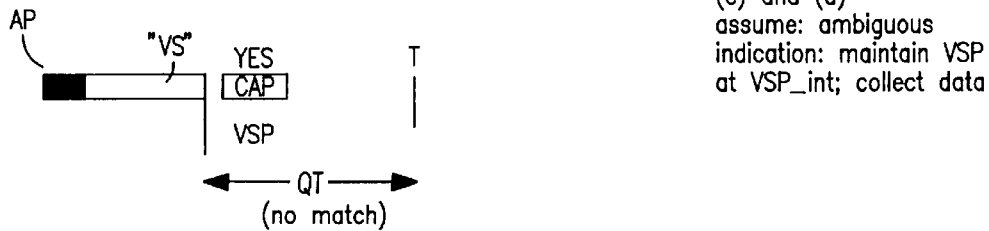

Referring now to FIG. 3, there is shown a flow diagram of a specific routine for determining when and how a VSP is to be delivered. The routine of FIG. 3 illustrates a test which is run by the pacemaker, to gather data and to determine from that data how best to respond to senses that occur within a programmable VSP_int (illustrated in FIG. 4). The test may be initiated automatically, or by external programming. Assuming that the test is on, a VSP is to be delivered on an early sensed signal from the ventricle only following an AP, since this is the situation when there may be crosstalk which cannot be distinguished from a true VS. Consequently, as indicated at 32, if there has not been an AP, the routine exits. If there has been an AP, at 33 the pacemaker compares the time from the AP to the VS to see whether it has fallen within the VSP_int. The VSP_int is set at a programmable value, e.g., 100 ms. If the AP-VS interval is not less than VSP_int, then the sensed signal is presumed to be a normal VS, and the routine exits. However, if the answer at 33 is yes, at 35 it is determined whether a VSP test is ongoing, in other words, whether the pacemaker is gathering information in order to make a determination as to how to respond to early ventricular senses.

If the pacemaker is gathering information so as to determine the VSP status, it is looking to see what happens after a VSP is delivered. Note that there are two ways to determine whether the sensed signal was in fact a true VS. For a true VS, the VSP will not result in capture, as it is delivered while the ventricle is still refractory. Also, the T wave will be seen earlier than would be the case if the ventricle were captured by the VSP. On the other hand, if the "VS" was in fact crosstalk, then the delivered VSP will result in capture, and the T wave will occur after a delay which corresponds, or matches, the patient's normal QT interval which is monitored at block of FIG. 2, based on timing data from block 17 (FIG. 1). These situations are illustrated by the timing diagrams of FIG. 4, which supplement the flow diagram of FIG. 3.

Returning to FIG. 3, at 44 a VSP counter, initially set to zero, is incremented., to obtain a running count of VSP events. Then, at 45, the VSP is delivered at the timeout of the VSP_int, e.g., 100 ms after delivery of the AP. At 47, it is determined whether the delivered VSP resulted in capture, by seeing whether or not an evoked response is sensed during a capture detection window following delivery of the VSP. See also FIG. 4 for an illustration of the capture detection window. The capture detection window is timed out by the microprocessor, or alternately by dedicated hardware, and is used to turn on sense circuit 16 for the limited capture detection window interval, in a known manner. If there has been no capture detected, the capture flag is set FALSE at 48; if capture is found, the capture flag is set TRUE at 49. Then, at 50, the pacemaker waits and determines whether a T wave is detected. If no, this means that one of the two desired pieces of information is not available, resulting in the premise that the situation is ambiguous. Accordingly, the routine branches to block 58, and the percentage of "ambiguous" VSP events is updated.

Returning to block 50, if a T wave is detected (T-Sense), it is determined whether the Twave_int, i.e., the interval from the delivered VSP to the T wave, matches the normally measured QT interval for this patient, a value which is obtained on an ongoing basis following each normal stimulus delivery (as discussed in connection with FIG. 2). If there is a match, and there has been capture, this strongly indicates that the VSP was effective, such that the sensed "VS" was in fact crosstalk. The routine then goes to 52 and updates the percentage of VSP during crosstalk. If, at 51, there is either no QT wave_int match, or capture is FALSE, the routine goes to 55. If there is both an absence of T wave match and capture is FALSE, each of which suggests a true VS, the routine goes to block 56 and updates the percentage of VSP during intrinsic R-sense. If, however, either there is a T wave_int match or there was capture, the two pieces of data cannot support a premise of crosstalk or a true VS, and the routine goes to 58 and updates the percentage of ambiguous VSPs. Following a calculation at 52, 56 or 58, at 59 the routine updates the counter, and determines whether the test number N has been reached. If no, meaning that the pacemaker is to continue gathering data, the routine exits; if yes, VSP status is determined at 60. This determination may be made by any desired analysis of the data; in a simple implementation the highest percentage dominates as long as it exceeds a minimum value, e.g., 50%. In an alternate embodiment, the value of N may be incremented by "ambiguous" events, so that more data is gathered when a high percentage of ambiguous events are determined. Following determination of the VSP status, the test flag is set to FALSE, as shown at 62, and Count is reset to zero.

If the test is not ongoing, and the criteria are set, the routine goes to block 36 and determines whether the pacemaker logic directs delivery of a VSP. If no, meaning that prior data has indicated that such a sense is probably a true VS, and not crosstalk, the routine exits to normal VS handling (in FIG. 2, the VS branch is taken from block 25 to block 26). However, if yes, the routine goes to 38 and determines whether the VSP should be delivered following a normal AV delay. If yes, the established premise is that this has been crosstalk, and at 39 a normal VP is set for delivery at AV_int, and the routine exits for further handling (in FIG. 2, this corresponds to going from block 25 back to block 23, for time out of the normal AV_int). However, if at 38 the answer is no, which corresponds to the ambiguous situation, then at 40 the pacemaker sets the logic for delivery of a VSP at the timeout of VSP_int (in FIG. 2, this corresponds to going from block 25 to block 27, for recalculation of the AV_int to time out at the end of VSP_int).

Referring specifically to FIG. 4, there are illustrated four timing diagrams which present different situations relating to a VS during the VSP_int, and the resulting assumptions. In timing diagram (a), the VSP window is shown starting after a short blanking period, and extending to a time VSP_int following the AP. A VSP is delivered at the end of VSP_int, and a capture detection window is timed out after a brief pause, during which the ventricular sense circuit 16 looks for an evoked response. Following this, the T wave is detected, and the QT, or VSP-T interval is determined, and compared to the stored value of QT to see if it matches. In this first example, there is capture AND a QT match, indicating that the VSP resulted in capture; consequently the assumption is that the "VS" was in fact crosstalk. This indicates that the best response to future "VS" events will be ignoring the VS and delivering a normal VP on a normal AV_int following the AP. Of course, if another VS intervenes, the normal VP is inhibited.

Referring to timing diagram (b), here there is neither sensed capture during the capture detection window, or a QT match. Note that the T wave is shown as arriving well earlier than in diagram (a), illustrating that the T wave likely did not result from the VSP. The conclusion is that a real VS has occurred, and that such VS events within the VSP_int should not be followed by a VSP. It is also noted that the T-wave following a sense event (VS) has a different morphology compared with one that follows a paced event (VP). This difference in T-wave morphology (VS-TS vs. VP-TS) can be used as another decision criteria. Where three such decision criteria are used, each can be given a predetermined priority for use in the determination made at block 60 of FIG. 3.

Referring to timing diagram (c), there is no evoked response detected in the capture detection window, but the QT matches; in diagram (d), there is an evoked response in the capture detection window, but no QT match. In both of these cases, there are cross-indications, so the situation is ambiguous, leaving the conclusion that delivery of VSP should be maintained at VSP_int while more data is collected.

There has thus been provided a system and method of automatically controlling when a VSP is to be delivered, and when it is not to be delivered; and for adjusting the timing of the VSP when it is to be delivered. It is to be recognized that the method of determining when early signals are to be recognized as representing true R waves or just crosstalk is illustrative, and variations of the algorithm for making such determination are within the scope of the invention. The testing for making the determination may be initiated by external programming, or may be programmed to be done periodically, e.g., every day or every week.

What is claimed is:

1. A dual chamber cardiac pacing system for pacing a patient, comprising;

AP means for generating and delivering atrial pace pulses to the patient's atrium;

AS means for sensing spontaneous atrial signals;

VP means for generating and delivering ventricular pace pulses to the patient's ventricle;

VS means for sensing ventricular signals;

timing means for timing out a predetermined VSP interval following a delivery of an atrial pace pulse;

said VP means comprising ventricular safety pulse (VSP) means for delivering a ventricular safety pulse at a predetermined time interval following a delivered atrial pace pulse when a ventricular signal has been sensed within said VSP interval;

data means for acquiring data reflective of the results of delivering ventricular safety pulses; and VSP control means for enabling said VSP means as a function of said acquired data;

wherein said VS means comprises means for sensing evoked R waves following delivered ventricular safety pulses, and said data means comprises means for determining whether a delivered ventricular safety pulse evoked an R wave as would result from capture by said ventricular safety pulse; and, wherein said data means comprises means for compiling data relating to whether delivered safety pulses are resulting in capture.

2. The system as described in claim 1, wherein said VSP control means comprises processing means for processing said data to determine whether such data indicates a high confidence that delivered ventricular pace pulses are resulting in capture, and enable means for enabling production of ventricular safety pulses when said data indicates such high confidence of capture.

3. The system as described in claim 2, wherein said processing means comprises means for processing said data to determine whether such data indicates with a high confidence that delivered ventricular pace pulses are not resulting in capture, and disable means for disabling production of ventricular safety pulses when said data indicates such high confidence of not capture.

4. The system as described in claim 1, wherein said VS means comprises VSP-T means for determining the VSP-T interval following a ventricular safety pulse, and said data means comprises means for determining whether a delivered ventricular safety pulse resulted in a normal VSP-T interval as indicates capture by said ventricular safety pulse.

5. The system as described in claim 4, wherein said data means comprises means for compiling data relating to whether delivered ventricular safety pulses evoked R waves and whether said pulses resulted in VSP-T intervals which indicate capture.

6. The system as described in claim 5, wherein said VSP control means comprises processing means for processing said data to determine whether such data indicates with a high confidence that delivered ventricular pace pulses are resulting in capture, and enabling means for enabling production of ventricular pace pulses when aid data indicates such high confidence of capture.

7. The system as described in claim 6, comprising AV means operative when production of ventricular pace pulses is enabled for controlling delivery of a ventricular safety pulse at a predetermined AV interval following a ventricular sense during said VSP interval.

8. The system as described in claim 6, wherein said processing means comprises means for processing said data to determine whether such data indicates with a high confidence that delivered ventricular pace pulses are not resulting in capture, and disabling means for disabling production of ventricular pace pulses when said data indicates such high confidence of no capture.

9. A dual chamber pacemaker system for pacing a patient, having a ventricular safety pulse (VSP) feature, comprising:

atrial pulse means for generating and delivering atrial pace pulses;

ventricular sensing means for sensing signals from the patient's ventricle;

"VS" detection means for detecting a said sensed signal that occurs within a predetermined VSP interval following a delivered atrial pace pulse as a "VS";

recognition means for collecting data following a plurality of "VS" detections, said data being indicative of whether or not such "VS" signals represented spontaneous R waves or were the result of crosstalk from the delivered atrial pace pulses, and for determining from said data when a "VS" is to be recognized as a spontaneous R wave and when it is to be recognized as a result of crosstalk;

controllable VSP means for generating and delivering a VSP to the patient's ventricle following a "VS" when said recognition means recognizes a said "VS" as being a result of crosstalk, and for inhibiting delivery of a VSP following a "VS" when said recognition means recognizes a said "VS" as a spontaneous R wave; wherein said recognition means comprises ambiguous means for determining when said data is ambiguous in terms of indicating whether said "VS" signals represent spontaneous R waves or are the result of crosstalk, and wherein said controllable VSP means comprises interval means for generating and delivering a VSP at a predetermined interval after each said "VS" when said data is ambiguous.

10. The system as described in claim 9, wherein said interval means comprises VSP_int means for controlling generation of said VSP at said VSP interval after each said "VS".

11. The system as described in claim 9, comprising mode means for placing said pacemaker in a VSP data gathering mode and while in said mode for controlling said controllable VSP means to generate and deliver a VSP at said VSP interval following each said "VS" and wherein said mode means controls said data means to be operative only during said data gathering mode.

12. The system as described in claim 9, wherein said recognition means comprises percentage means for determining from said data the percentage of delivered "VS" events where a spontaneous R wave is indicated and the percentage of delivered "VS" events where crosstalk is indicated.

13. In a dual chamber pacemaker system, a method of automatically determining the likely nature of an early ventricular sense and responding appropriately, comprising:

placing said system in a data gathering modes and collecting data after each early ventricular sense relating to whether each said early sense was crosstalk or an intrinsic ventricular beat;

analyzing said data and determining the probable nature of said early senses; and setting said pacemaker to either deliver a ventricular safety pulse (VSP) or to start a next cycle without delivery of a ventricular pace pulse depending upon said analyzing;

wherein during said gathering mode of said pacemaker system performs the steps of delivering a VSP following each said early ventricular sense, and monitoring to detect at least one ventricular wave portion following delivery of each said VSP, and wherein said monitoring comprises detecting whether each said delivered VSP resulted in capture and determining the QT interval following said each VSP.

14. A dual chamber pacemaker system for pacing a patient, said system having an implantable pacemaker, said pacemaker having AP means for generating atrial pace pulses for delivery to the patient's atrium and VP means for generating ventricular pace pulses to the patient's ventricle, and lead means for delivering pacing pulses from said pacemaker to the patient's heart and for delivering sensed natural signals from at least the patient's ventricle to said pacemaker, comprising:

early sense means for determining when an early ventricular sense occurs within a predetermined time interval following delivery of an atrial pace pulse;

data means for obtaining data reflective of whether such early senses reflect natural R waves or are due to crosstalk; and AV means enabled when said data are reflective of crosstalk for controlling delivery of a ventricular pace pulse at a normal AV interval following a said early sense; wherein said data means comprises means for indicating when said data is statistically ambiguous in indicating whether said early senses are reflective of natural R waves or crosstalk, and ventricular safety pulse (VSP) control means for controlling said VP means to deliver a ventricular safety pulse following said early sense only when said data is indicated as ambiguous.

15. The system as described in claim 14, comprising normal means for handling a said early sense as a natural R wave when said data indicates that said early senses reflect natural R waves.

* * * * *